United States Patent
Ortega et al.

(10) Patent No.: US 10,960,123 B2
(45) Date of Patent: Mar. 30, 2021

(54) PERITONEAL DIALYSIS SYSTEMS AND RELATED METHODS

(71) Applicant: Fresenius Medical Care Holdings, Inc., Waltham, MA (US)

(72) Inventors: Anthony Thomas Ortega, Antioch, CA (US); Nicolas Huntington, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 95 days.

(21) Appl. No.: 16/018,725

(22) Filed: Jun. 26, 2018

(65) Prior Publication Data

US 2019/0388602 A1    Dec. 26, 2019

(51) Int. Cl.
*A61M 1/28* (2006.01)

(52) U.S. Cl.
CPC ........... *A61M 1/28* (2013.01); *A61M 2205/18* (2013.01); *A61M 2205/332* (2013.01); *A61M 2205/3368* (2013.01); *A61M 2205/3393* (2013.01); *A61M 2205/36* (2013.01); *A61M 2205/50* (2013.01); *A61M 2205/581* (2013.01); *A61M 2205/583* (2013.01)

(58) Field of Classification Search
CPC .......... A61M 5/44; A61M 1/166; A61M 1/28; A61M 2205/50; A61M 2205/581; A61M 2205/36; A61M 2205/18; A61M 2205/12; A61M 2205/3393; A61M 2205/583; A61M 2205/3368; A61M 2205/332
USPC ........................................................ 177/154
See application file for complete search history.

(56) References Cited

U.S. PATENT DOCUMENTS

| | | | |
|---|---|---|---|
| 5,141,493 A * | 8/1992 | Jacobsen | A61M 1/1696 210/104 |
| 7,207,966 B2 | 4/2007 | Savare et al. | |
| 7,789,850 B2 | 9/2010 | Roger | |
| 7,935,074 B2 | 5/2011 | Plahey et al. | |
| 9,180,240 B2 | 11/2015 | Farrell et al. | |
| 9,585,992 B2 | 3/2017 | Bene | |
| 2002/0032403 A1 | 3/2002 | Savagle et al. | |
| 2006/0195064 A1 | 8/2006 | Plahey et al. | |
| 2008/0058712 A1 | 3/2008 | Plahey | |
| 2008/0177222 A1 | 7/2008 | Roger | |
| 2009/0009179 A1 | 1/2009 | Sobue et al. | |

(Continued)

FOREIGN PATENT DOCUMENTS

| | | |
|---|---|---|
| CN | 102802693 | 11/2012 |
| CN | 104174081 | 12/2014 |

(Continued)

OTHER PUBLICATIONS

Honeywell, Force Sensors Line Guide 2017, 5 pages.

(Continued)

*Primary Examiner* — Jacques M Saint Surin
(74) *Attorney, Agent, or Firm* — Fish & Richardson P.C.

(57) ABSTRACT

In one aspect, a peritoneal dialysis system includes a tray for supporting a bag that can receive dialysate from a source of dialysate, multiple force sensors disposed adjacent a portion of the tray that is in contact with the bag when the bag is supported by the tray, and one or more processors configured to receive data from the multiple force sensors and to determine, based on the data, an amount of dialysate contained in the bag.

23 Claims, 10 Drawing Sheets

(56) References Cited

U.S. PATENT DOCUMENTS

| | | |
|---|---|---|
| 2009/0299273 A1 | 12/2009 | Lee et al. |
| 2011/0186517 A1 | 8/2011 | Hedmann et al. |
| 2011/0315611 A1 | 12/2011 | Filkerson |
| 2013/0006171 A1 | 1/2013 | Griessmann |
| 2014/0199057 A1 | 7/2014 | Hansen et al. |
| 2015/0129499 A1 | 5/2015 | Bene |
| 2015/0144543 A1 | 5/2015 | Kondo |
| 2017/0014566 A1* | 1/2017 | Childers .............. A61M 1/28 |
| 2017/0072124 A1* | 3/2017 | James ................ A61M 1/282 |
| 2017/0281845 A1* | 10/2017 | Manda .............. A61K 31/716 |
| 2017/0304519 A1* | 10/2017 | Jonas ................ A61M 1/1607 |
| 2019/0083692 A1* | 3/2019 | Plahey .............. A61M 1/284 |

FOREIGN PATENT DOCUMENTS

| | | |
|---|---|---|
| CN | 104602378 | 5/2015 |
| DE | 102012006149 | 3/2012 |
| JP | 2008241415 A * | 10/2008 |
| WO | WO 2008/106452 | 9/2008 |
| WO | WO 2009/148987 | 12/2009 |

OTHER PUBLICATIONS

Honeywell, Sensors in Hemodialysis Machines, An Application Note 2016, 6 pages.

International Preliminary Report on Patentability in International Application No. PCT/US2016/048306, dated Mar. 13, 2018, 8 pages.

International Search Report and Written Opinion in Application No. PCT/US2016/048306, dated Nov. 14, 2016, 12 pages.

Liberty Cycler User's Guide 2011-2012, 226 pages.

Vecchi et al., "Experimental Evaluation of Two Commercial Force Sensors for Applications in Biomechanics and Motor Control", 5$^{th}$ Ann Conf of Int FES Jun. 2000.

International Search Report and Written Opinion in Application No. PCT/US2019/035532, dated Aug. 23, 2019, 12 pages.

CN Office Action in Chinese Appln. No. 201680052833.X, dated Apr. 1, 2020, 12 pages (with English translation).

* cited by examiner

PERITONEAL DIALYSIS SYSTEMS AND RELATED METHODS

TECHNICAL FIELD

This disclosure relates to peritoneal dialysis (PD) machines, and more particularly to weighing dialysate solution contained within heater bags that are supported by PD machines.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

The cyclers are designed to manage a number of bags each typically containing up to 5 liters of dialysate. The dialysate is then pumped by the machine or, in so-called gravity systems, allowed by the machine to flow through a patient line to the patient. But, to avoid thermal shock, the dialysate is heated first to near the patient's body temperature before infusion.

One technique for heating the dialysate is to place a dedicated heater bag on top of a heater tray, equipped with heating coils and a temperature sensor. In this arrangement, all fluid delivered to the patient comes from the heater bag. During a dwell period, the heater bag can be refilled from one of several heater bags connected to the machine and warmed so that it will be ready to supply the next fill to the patient.

SUMMARY

This disclosure relates to weighing dialysate solution contained within heater bags disposed atop heater trays of peritoneal dialysis (PD) machines.

In one aspect, a PD system includes a tray for supporting a bag that can receive dialysate from a source of dialysate, multiple force sensors disposed adjacent a portion of the tray that is in contact with the bag when the bag is supported by the tray, and one or more processors configured to receive data from the multiple force sensors and to determine, based on the data, an amount of dialysate contained in the bag.

Implementations may include one or more of the following features.

In some implementations, the multiple force sensors are arranged in an array that spans a majority of a cross-sectional area of the tray.

In some implementations, the multiple force sensors include thin film sensors that are secured to the tray with an adhesive.

In some implementations, the multiple force sensors are attached to a top surface of the tray.

In some implementations, the multiple force sensors are disposed within a body of the tray adjacent a top surface of the tray.

In some implementations, the multiple force sensors are arranged to provide a weight distribution of dialysate within the bag across the tray.

In some implementations, the one or more processors are further configured to determine, based on the data, whether or not the bag is appropriately located on the tray.

In some implementations, the data includes output values corresponding to measureable weights from at least a threshold number of the plurality of force sensors.

In some implementations, the one or more processors are further configured to determine, based on the data, whether or not the bag is supported by the tray.

In some implementations, the data includes output values from each of the plurality of force sensors that are equal to a reference value.

In some implementations, the one or more processors are further configured to calculate the amount of dialysate contained in the bag from the data according to an algorithm.

In some implementations, the one or more processors are further configured to determine the amount of dialysate contained in the bag by summing values included in the data.

In some implementations, the one or more processors are further configured to compare the amount of dialysate to a reference amount.

In some implementations, the one or more processors are further configured to trigger an alarm if a difference between the amount of dialysate and the reference amount exceeds a threshold amount.

In some implementations, the alarm includes a visual or an audio notification. In some implementations, the tray includes a heating element configured to heat the tray.

In some implementations, the tray is configured to conduct heat such that the tray heats the bag when the bag is supported by the tray.

In some implementations, the tray includes one or more temperature sensors configured to detect a temperature of the bag.

In some implementations, the tray defines a receptacle configured to receive the bag.

In some implementations, the PD system further includes the source of dialysate.

In another aspect, a method of determining an amount of dialysate in a bag includes flowing dialysate from a source to a bag supported on a tray, sending data to one or more processors from multiple force sensors disposed adjacent a portion of the tray that is in contact with the bag, and determining, via the one or more processors, an amount of dialysate contained in the bag based on the data.

Implementations may provide one or more of the following advantages.

In some implementations, an arrangement of force sensing elements (e.g., laid out in a two-dimensional (2D) array across a top surface of a heater tray) can provide a weight distribution across the heater tray that can advantageously be used to determine whether or not the heater bag is appropriately placed atop the heater tray, whereas conventional weight scales used in other dialysis systems may be limited to merely providing a measurement of total weight atop a heater tray. In some implementations, determining an appropriate placement of the heater bag in conjunction with determining the amount of dialysate within the heater bag at any point in time can improve an overall assessment of the heater bag and therefore streamline operator interaction with a PD system during treatments. Such streamlined interaction can reduce inconveniences for a patient or an operator and accordingly minimize returns or troubleshooting of the PD system that could otherwise occur.

Additionally, positioning of the force sensing elements across the top surface of the heater tray can advantageously remove the requirement for a conventional weight scale (e.g., a load cell) that may otherwise be disposed between a housing of the PD system and a bracket supporting the heater tray. Since such weight scales are often subject to shipping and handling damage, removal of such weight scales can significantly reduce the risk of damage to the PD system during transportation and any associated costs or inconveniences.

Other aspects, features, and advantages will be apparent from the description, the drawings, and the claims.

DESCRIPTION OF DRAWINGS

Like reference symbols in the various drawings indicate like elements.

DETAILED DESCRIPTION

A dialysis machine, such as a peritoneal dialysis (PD) machine, can be configured to detect whether a heater bag containing dialysate is present and is being heated correctly. A PD machine typically includes a heater tray on which the dialysate heater bag is placed to warm up the dialysate in the bag. If the tray contains heat sensors such as thermistors, a component of the dialysis machine can measure the output of the heat sensors over time to determine if the heater bag is present on the tray and if the heater bag is correctly positioned on the tray. For example, if the output of the heat sensors indicates that the tray is heating up too quickly, then the bag may not be absorbing heat from the tray correctly or the bag may not be present to absorb any heat at all. In response, the dialysis machine could display a message to a user indicating that the bag is positioned incorrectly or is absent.

Figure 1:
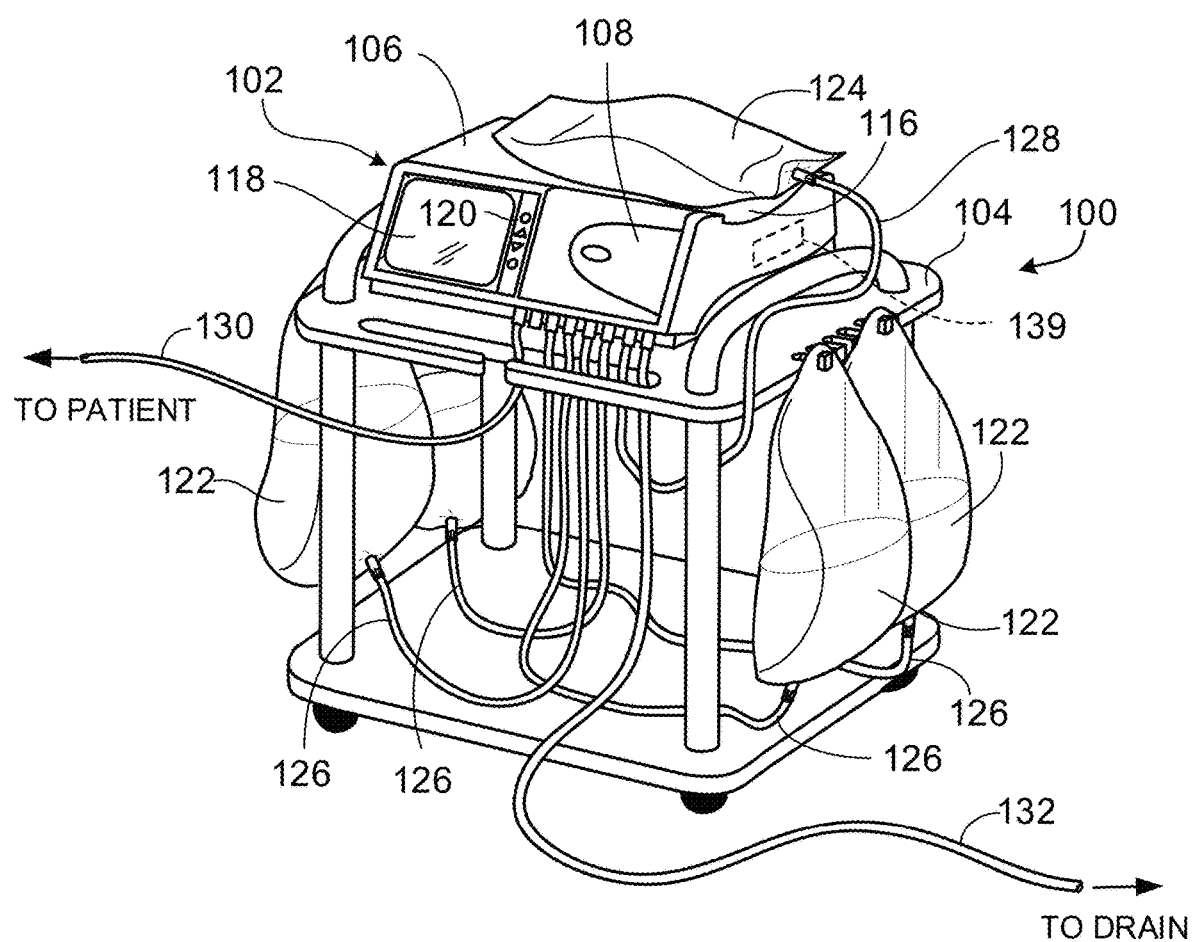
FIG. 1 is a perspective view of a peritoneal dialysis (PD) system.
Figure 2:
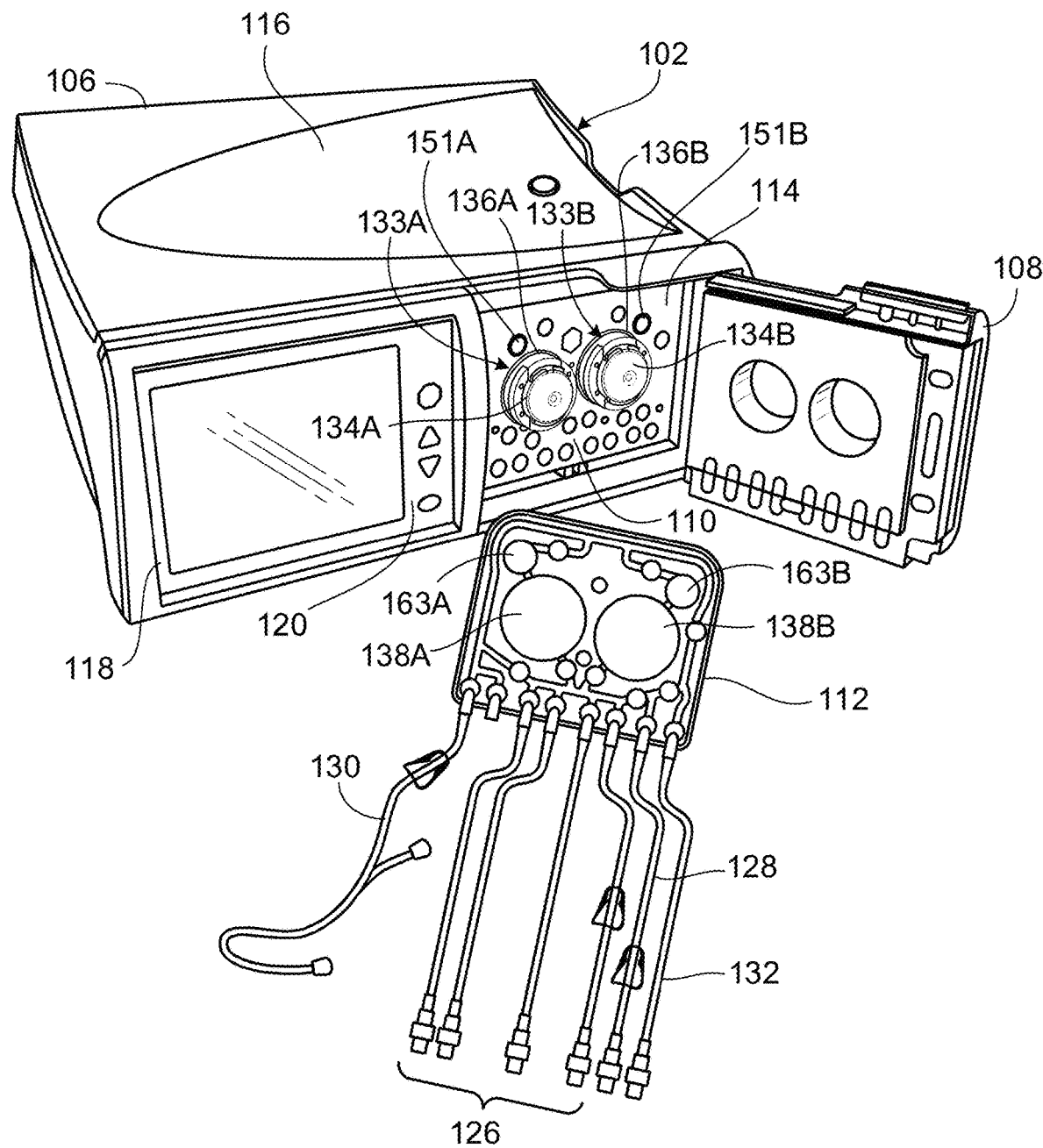
FIG. 2 is a perspective view of a PD cycler of the PD system of FIG. 1.

Referring to FIG. 1, a PD system 100 includes a PD cycler 102 (also referred to as a PD machine) seated on a cart 104. Referring also to FIG. 2, the PD cycler 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 120 that can be operated by a user (e.g., a patient) to allow, for example, set-up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The drain line 132 can be connected to a drain or drain receptacle and can be used to pass dialysate from the cassette 112 to the drain or drain receptacle during use.

Figure 3:
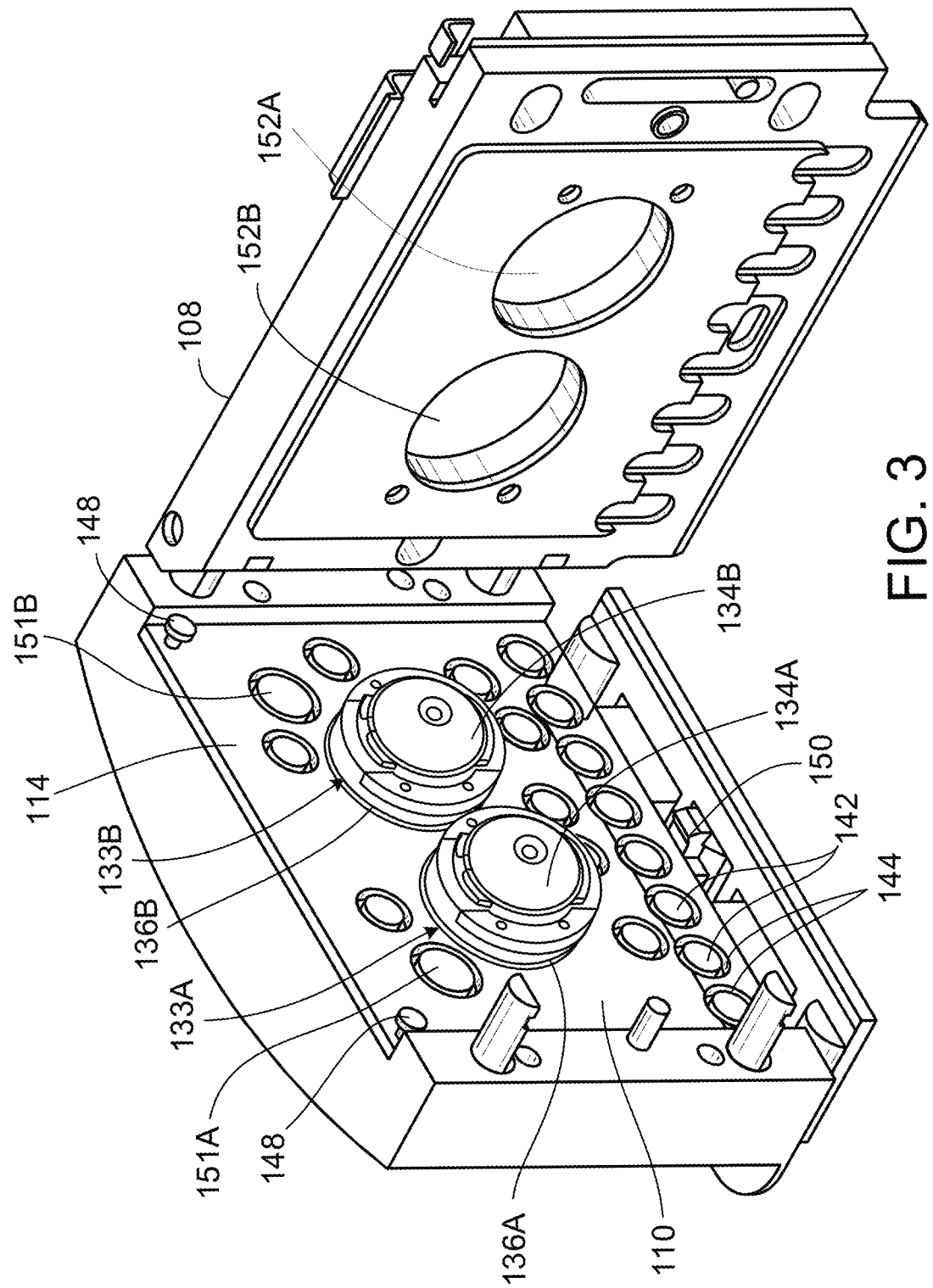
FIG. 3 is a perspective view of a cassette interface of the PD cycler of FIG. 2.

FIG. 3 shows a more detailed view of the cassette interface 110 and the door 108 of the PD cycler 102. As shown, the PD cycler 102 includes pistons 133A, 133B with piston heads 134A, 134B attached to piston shafts 135A, 135B (piston shaft 135A shown in FIG. 4) that can be axially moved within piston access ports 136A, 136B formed in the cassette interface 110. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The nuts, in turn, are connected to the pistons 133A, 133B and thus cause the pistons 133A, 133B to move inward and outward as the stepper motors rotate the lead screws. Stepper motor controllers provide the necessary current to be driven through the windings of the stepper motors to move the pistons 133A, 133B. The polarity of the current determines whether the pistons 133A, 133B are advanced or retracted. In some implementations, the stepper motors require 200 steps to make a full rotation, and this corresponds to 0.048 inch of linear travel.

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to accurately position the piston heads 134A, 134B of the pistons 133A, 133B.

When the cassette 112 (shown in FIG. 2) is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to dome-shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIG. 2) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B.

The pressure sensors 151A, 151B can be any sensors that are capable of sensing the fluid pressure in the sensing chambers 163A, 163B. In some implementations, the pressure sensors are solid state silicon diaphragm infusion pump force/pressure transducers. One example of such a sensor is the Model 1865 force/pressure transducer manufactured by Sensym Foxboro ICT. In certain implementations, the force/pressure transducer is modified to provide increased voltage output. The force/pressure transducer can, for example, be modified to produce an output signal of 0 to 5 volts.

Still referring to FIG. 3, the PD cycler 102 also includes multiple inflatable members 142 positioned within inflatable member ports 144 in the cassette interface 110. The inflatable members 142 align with depressible dome regions (not shown) of the cassette 112 when the cassette 112 is positioned within the cassette compartment 114 of the PD cycler 102. Dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD cycler 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD cycler 102, as shown in FIG. 3, defines cylindrical recesses 152A, 152B that substantially align with the pistons 133A, 133B when the door 108 is in the closed position. When the cassette 112 is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

A control unit 139 (e.g., a microprocessor, shown in FIG. 1) is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. In some implementations, the control unit 139 is an MPC823 PowerPC device manufactured by Motorola, Inc.

The control unit 139 monitors the components to which it is connected to determine whether any complications exists within the PD system 100. In the event of complications, the control unit 139 triggers one or more alarms which warn a patient or operator of the PD system 100 of conditions, e.g., conditions requiring attention from the patient or operator. The alarms can include audio alerts (e.g., generated by a speaker), visual alerts (e.g., displayed on touch screen 118), or other types of alerts.

One such condition for triggering an alarm is a state of the heater tray 116 and heater bag 124. For example, if the heater tray 116 or heater bag 124 requires attention from a patient or operator, an alarm may be triggered. The heater tray 116 or heater bag 124 requires attention if the heater bag 124 is positioned incorrectly on the heater tray 116, if the heater bag 124 is absent from the heater tray 116, or if heater bag 124 contains an amount of dialysate that is outside of a permissible range of dialysate. In some implementations, the control unit 139 can determine if the heater 124 bag is positioned incorrectly or is absent based on measurements obtained using one or more temperature sensors such as thermistors. In some implementations, the control unit 134 can determine if the amount of dialysate in the heater bag 124 is out of range based on measurements using force sensors.

Figure 4:
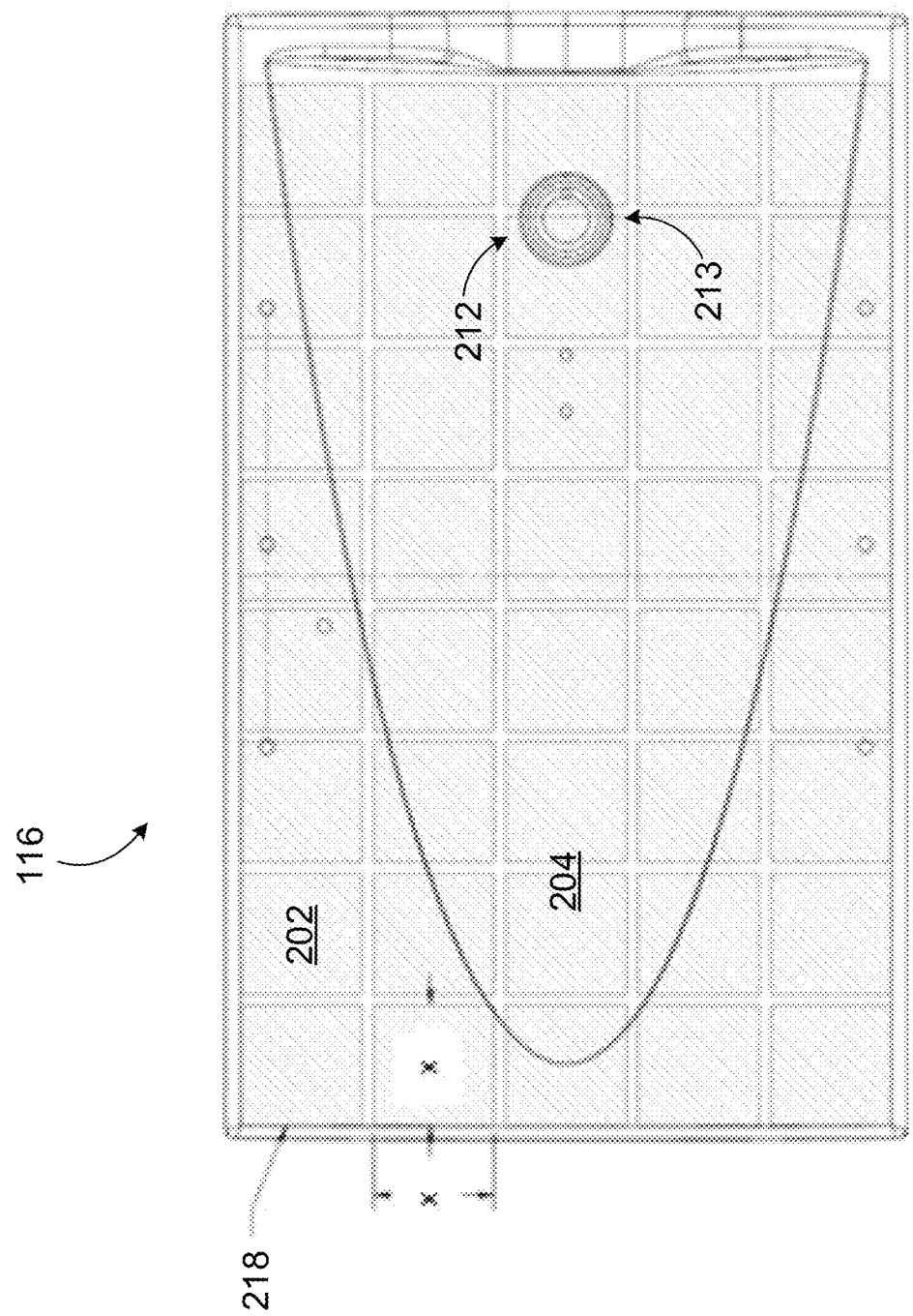
FIG. 4 is a top view of a heater tray of the PD cycler of FIG. 2.

FIGS. 4-8 show the heater tray 116 in detail. Referring to FIG. 4, a top surface 202 of the heater tray 116 defines a shallow concave indentation 204. The indentation 204 is sized and shaped to receive the heater bag 124 (shown in FIG. 1). When the heater bag 124 is placed at the indentation 204, the heater bag 124 is cradled by the indentation in a manner that increases the contact between the heater bag 124 and the top surface 202. In particular, the heater bag 124 is made of a pliable material that conforms to the shape of solid objects in contact with the heater bag 124. Thus, when the heater bag 124 is placed on the top surface 202 at the indentation 204, the heater bag 124 will conform to the shape of the indentation 204.

Figure 5:
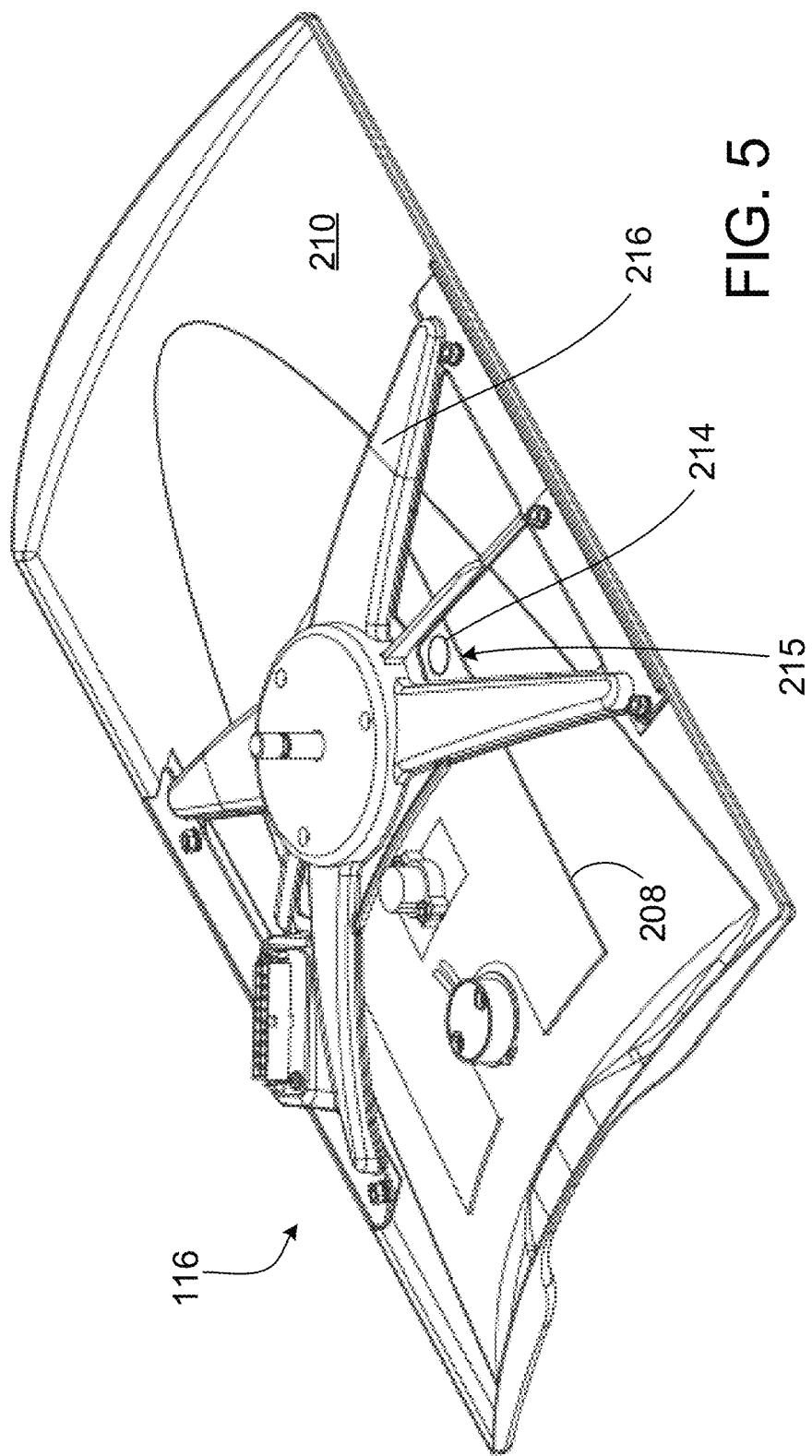
FIG. 5 is a bottom perspective view of the heater tray of FIG. 4.

Referring to FIG. 5, the heater tray 116 is supported along a bottom surface 206 by a bracket 216 that is designed to be positioned atop the housing 106 (shown in FIG. 1. The bottom surface 206 of the heater tray 116 is in contact with a surface of a heating element 208. The heating element 208 generates heat when electricity is applied to it. For example, electricity could be applied to the heating element 208 based on a control output from the control unit 139. When the heating element 208 generates heat, the heat is conducted by the body 210 of the heater tray 116. When heat is conducted by the body 210 of the heater tray 116, the indentation 204 will warm up and conduct heat to the heater bag 124.

Referring again to FIG. 4, the heater tray 116 includes at least one temperature sensing element 212 positioned along or near the top surface 202 of the heater tray 116. The sensing element 212 is used to measure a temperature of the heater tray 116, which can be indicative of the state of the heater tray 116 and/or the state of the heater bag. The temperature of the heater tray 116 can be used, in particular, to measure temperature changes that would indicate that the heater bag 124 is positioned incorrectly on the heater tray 116 or that the heater bag 124 is absent from the heater tray 116.

In some implementations, multiple temperature sensing elements are used. For example, as shown in FIG. 5, a second temperature sensing element 214 can be included along or near the bottom surface 206 of the heater tray 116. Accordingly, the second sensing element 214 can measure temperature change at a location that is different from the location of the first sensing element 212. The sensing element 212 is positioned to contact the heater bag 124 when the heater bag 124 is positioned correctly on the heater tray 116, whereas the sensing element 214 is positioned near, or contacts, the heating element 208. In this way, the measurements of the first sensing element 212 tend to be affected more than those of the second sensing element 214, depending on the position of the heater bag 124 on the heater tray 116. In contrast, the measurements of the sensing element 214 tend to be affected more than those of the first sensing element 212, depending on the presence or absence of the heater bag 124 (e.g., depending on how much heat generated by the heating element 208 is absorbed as the heating element 208 heats up).

An example of an element that measures temperature is a thermistor, which is a resistor having a resistance that varies with temperature in a manner that can be measured, e.g., when current flows through the thermistor. Thus, the voltage drop across the thermistor will vary according to temperature, and can be measured to determine a current temperature of the thermistor. While resistors other than thermistors sometimes have a resistance that varies with temperature, a thermistor tends to have a resistance that changes with temperature more significantly and/or more consistently than other types of resistors. In some implementations, the sensing elements 212, 214 can include one or more (e.g., two) thermistors.

In addition to the temperature sensing elements 212, 214, the heater tray 116 also includes multiple force sensing elements 218 arranged in a 2D array (e.g., a matrix) across the top surface 202 of the heater tray 116. The force sensing elements 218 are used to measure weights atop the heater tray 116 at respective locations of the force sensing elements 218, such that values output by the force sensing elements 218 correspond to a weight distribution of the heater bag 124 across the heater tray 116. The weight distribution can indicate one or more of a correct or incorrect positioning of the heater bag 124 on the heater tray 116, an amount of dialysate present in the heater bag 124, and an absence of the heater bag 124 from the heater tray 116.

In some implementations, the force sensing elements 218 are disposed on top of the top surface 202 of the heater tray 116, such that one or more of the force sensing elements 218 can be in direct contact with the heater bag 124 when the heater bag 124 is positioned atop the heater tray 116. In some implementations, the force sensing elements 218 are disposed on top of the top surface 202 of the heater tray 116, but protected with a cover, such that the force sensing elements 218 can be in close proximity to the heater bag 124 when the heater bag 124 is positioned atop the heater tray 116, yet not in direct contact with the heater bag 124. In some implementations, the force sensing elements 218 are embedded within the body 210 of heater tray 116 in close proximity to the top surface 202 (e.g., within about 0.1 cm to about 0.5 cm of the top surface 202) to protect the force sensing elements 218 from potential wear or damage, while still located close enough to the heater bag 124 to accurately detect the weight of the heater bag 124.

Figure 6:
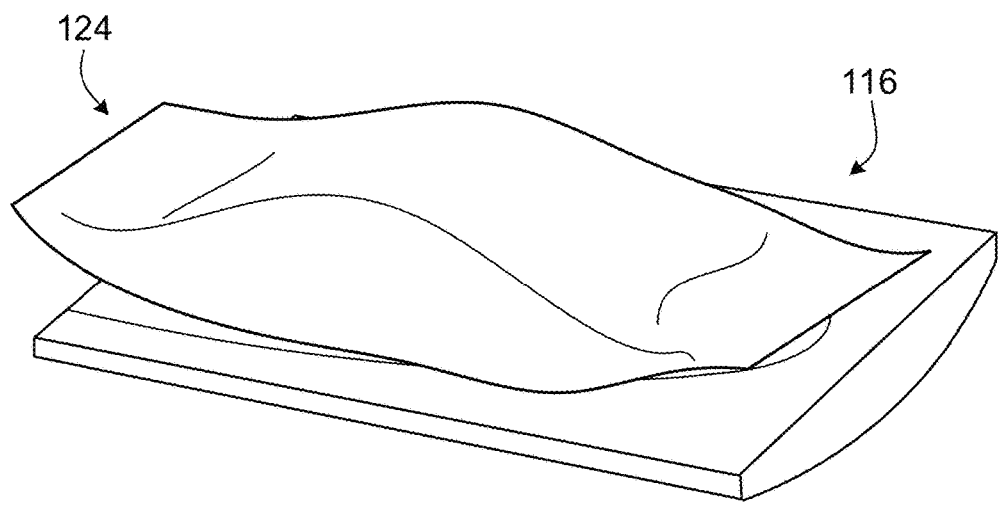
FIG. 6 is a perspective view of a heater bag placed appropriately atop the heater tray of FIG. 4.

For example, referring to FIG. 6, when the heater bag 124 is positioned correctly on the heater tray 116, most of a surface on a lower side of the heater bag 124 is in contact with the heater tray 116. In general, a heater bag 124 is correctly positioned on the heater tray 116 if a threshold amount of a surface of the heater bag 124 (e.g., 40% of the total surface) is in physical contact with the heater tray 116. According to such correct positioning, each of at least a threshold number (e.g., about 70%-80%) of contiguous force sensing elements 218 of the total number of force sensing elements 218 will output a value that corresponds to a respective weight of fluid within the heater bag 124 atop the force sensing element 218.

Figure 7:
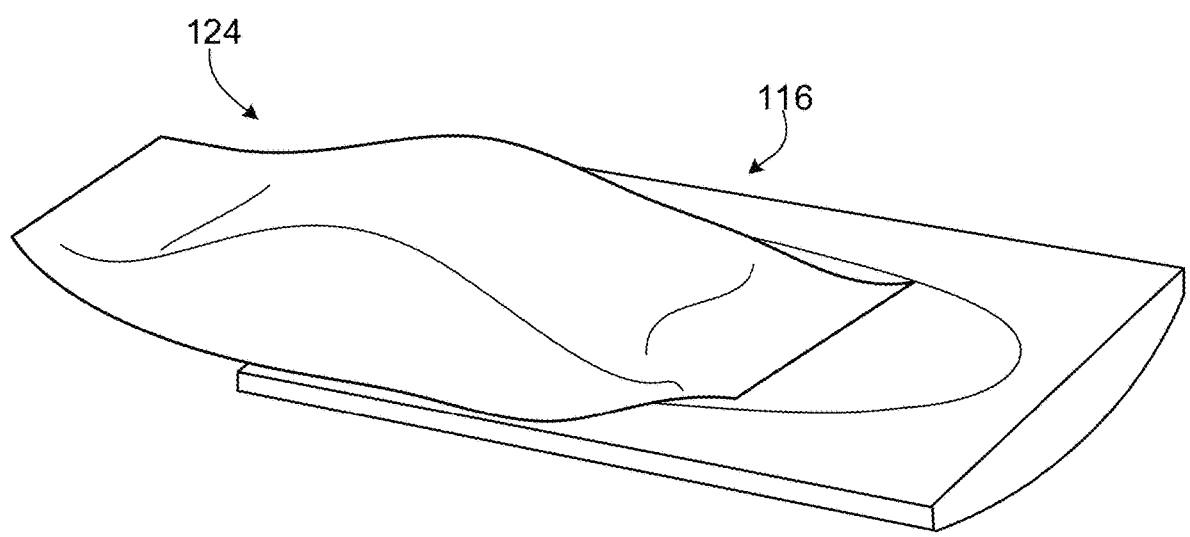
FIG. 7 is a perspective view of a heater bag placed inappropriately atop the heater tray of FIG. 4.

Referring to FIG. 7, in contrast, if the heater bag 124 is positioned incorrectly on the heater tray 116 (e.g., in a manner such that less than the threshold amount of the total surface of the heater bag 124 is in contact with the heater tray 116), then one or more, but fewer than the threshold number of contiguous force sensing elements 218 will detect a measurable weight and output corresponding values.

Figure 8:
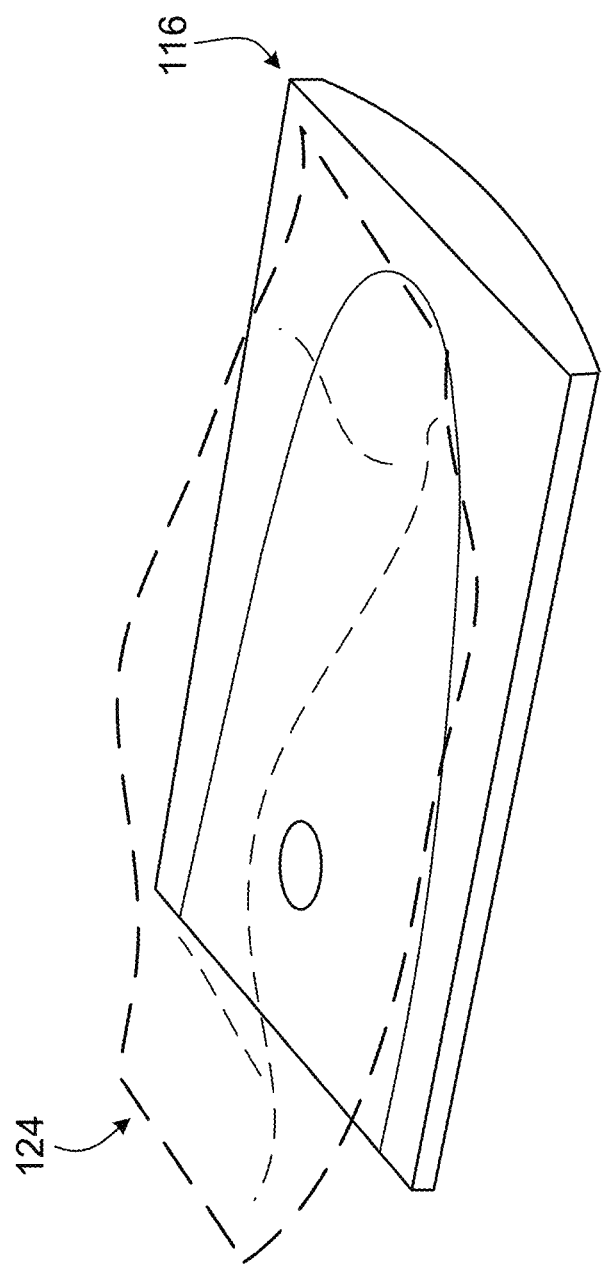
FIG. 8 is a perspective view of the heater tray of FIG. 4 without a heater bag.

Referring to FIG. 8, if the heater bag 124 is absent from the heater tray 116 (e.g., and no other mass is present atop the heater tray 116), then all of the force sensing elements 218 will output a reference value (e.g., corresponding to a weight of zero).

In some implementations, the force sensing elements 218 are piezo-resistors that output voltage values corresponding to respective weights detected by the force sensing elements 218. Furthermore, the force sensing elements 218 are provided as thin film sensors (e.g., having a thickness of about 0.2 mm or less and made of a flexible material) such that the force sensing elements 218 can conform to the top surface 202 of the heater tray 116. Example materials from which the force sensing elements 218 may be made include polyester and silicon, among other materials. In some implementations, the force sensing elements 218 are secured to the top surface 202 or to an interior region of the body 210 that is adjacent the top surface 202 with an adhesive, such as various epoxy adhesives. In some implementations, the force sensing elements 218 have a rectangular (e.g., square) shape. The force sensing elements 218 typically have a length and a width x in a range of about 50 cm to about 300 cm and typically have a thickness in a range of about 0.2 mm to about 0.3 mm. A spacing between edges of adjacent force sensing elements 218 is typically in a range of about 0.1 cm to about 0.2 cm. In some implementations, the total number of force sensing elements 218 is in a range of 20 to 40, where a greater number of force sensing elements 218 provides a finer resolution of the weight distribution across the heater tray 116, while a lesser number of force sensing elements 218 provides a coarser resolution of the weight distribution across the heater tray.

Figure 9:
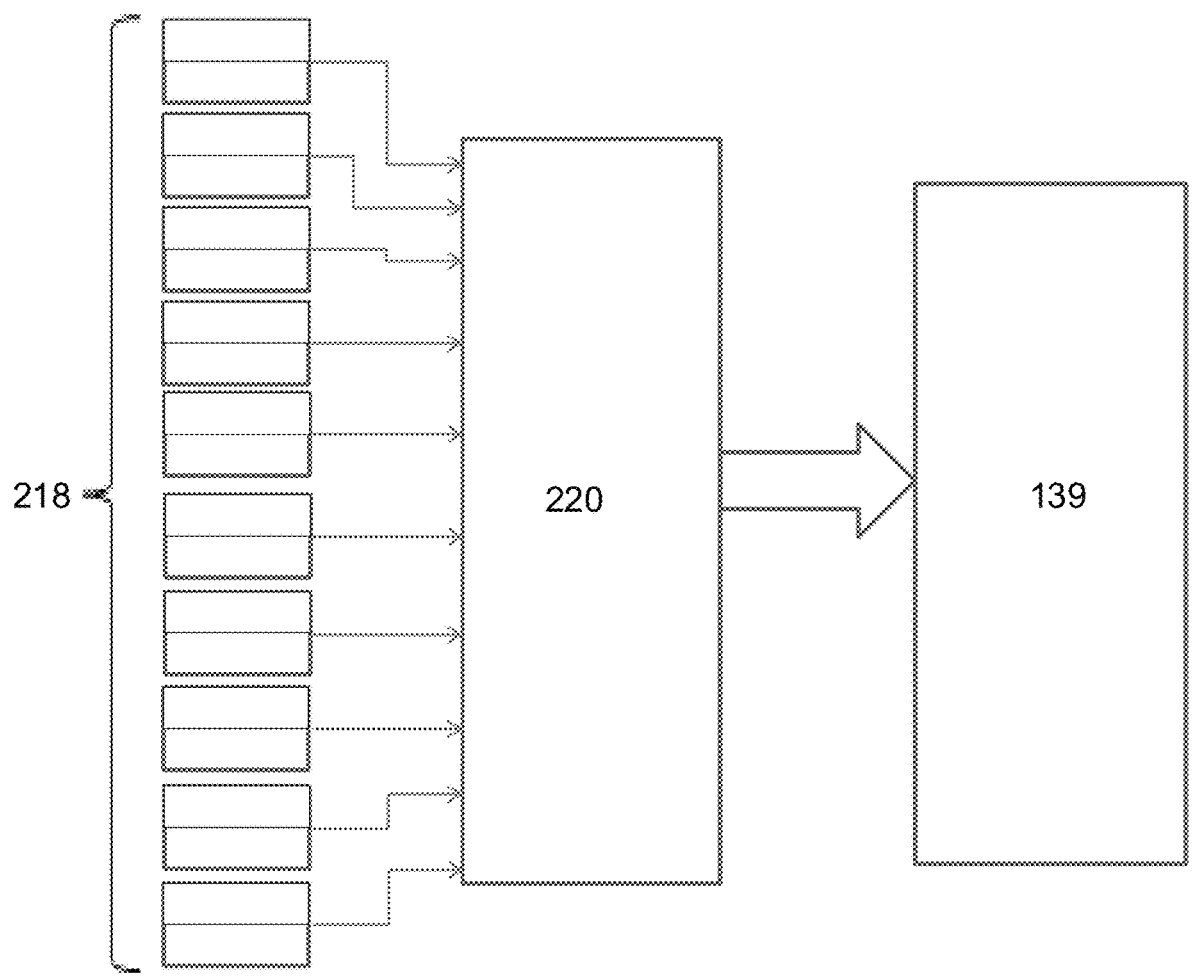
FIG. 9 is a schematic diagram of an analog-to-digital converter of the PD system of FIG. 1.

Referring to FIG. 9, the control unit 139 is in communication with the force sensing elements 218 (e.g., as well as the temperature sensing elements 212, 214 discussed above) and calculates weights based on signals received from the force sensing elements 218. For example, the force sensing elements 218 output analog signals (e.g., voltage values) to an analog-to-digital converter (ADC) 220, which then coverts the analog signals to digital signals (e.g., voltage values) and sends the digital signals to the control unit 139. The control unit 139 can execute an algorithm (e.g., including a mathematical equation) stored in memory to calculate weights from the digital signals received from the ADC 220. In some implementations, the force sensing elements 218 are controlled to output signals at a predetermined frequency (e.g., once every 0.1 seconds). Additionally, the control unit 139 can access positions (e.g., 2D array positions) of the force sensing elements 218 across the top surface 202 of the heater tray 116 from a data structure store in memory.

When the heater bag 124 is correctly positioned on the heater tray 116 (e.g., when the control unit 139 receives values corresponding to measurable weights from a threshold number of force sensing elements 218 whose locations are determined as contiguous from positional data stored in the data structure), the control unit 139 can calculate an amount of dialysate contained within the heater bag 124 based on a sum (e.g., a simple sum) of the weights detected by the force sensing elements 218. In some implementations, the calculation may be modified by a scaling or weighting factor or modified by an addition or subtraction parameter. In some implementations, the amount of dialysate can be quantified as a weight (e.g., quantified in newtons or pounds), a mass (e.g., quantified in kilograms based on a conversion factor applied to the weight), or a volume (e.g., quantified in liters based on a conversion factor applied to the weight).

For each time point at which the force sensing elements 218 output a signal, the control unit 139 can compare the total amount of dialysate contained within the heater bag 124 to a known reference amount (e.g., a desired or set point amount) associated with the time point. In some implementations, the reference amount can be based on a volume capacity (e.g., 2 L, 3 L, or 5 L) of the heater bag 124 and/or an amount of dialysate delivered to the patient. If an absolute value of a difference between the total amount of dialysate contained within the heater bag 124 and the reference amount is greater than a predetermined value for more than a predetermined number of time points within a predetermined period, then the control unit 139 triggers an alarm (e.g., a visual or an audio notification) to indicate to a patient or an operator that one or more actions should be performed to address the discrepancy. Such actions can include stopping and restarting the treatment. In some implementations, the alarm may serve as a warning for which a message is displayed to a patient in which the patient is asked to confirm continuation of treatment. In some examples, upon triggering the alarm, the control unit 139 also sends an instruction to a safety clamp associated with the patient line 130 (shown in FIG. 1) to close off the patient line 130 to prevent further dialysate fluid flow between the patient's abdominal cavity and the PD system 100. Upon a restart of the treatment process and a proper placement of the heater bag 124 (e.g., as detected by the threshold number of contiguous force sensing elements 218), the safety clamp disengages the patient line 130 to permit dialysate fluid flow in the patient line 130.

Figure 11:
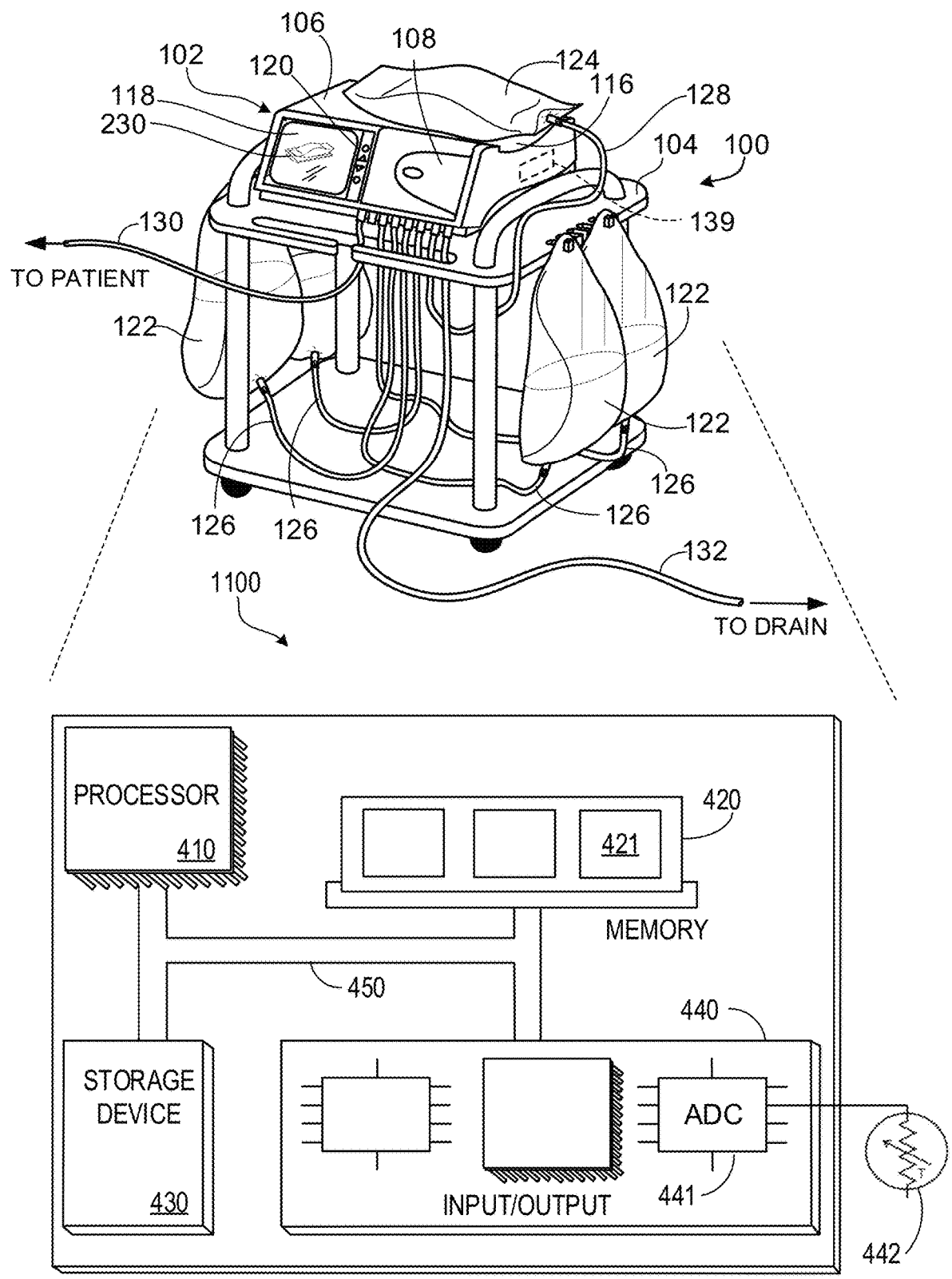
FIG. 11 is a block diagram of an example computer system by which a control unit of the PD system of FIG. 1 can be implemented.

When the heater bag 124 is incorrectly positioned on the heater tray 116 (e.g., when the control unit 139 receives values corresponding to measurable weights from one or more, but fewer than the threshold number of contiguous force sensing elements 218), the control unit 139 triggers an alarm to indicate to a patient or an operator that the heater bag 124 should be repositioned atop the heater tray 116. Flow in the patient line 130 may be cut off, and a treatment restart may be required. In some implementations, an image 230 is displayed on the screen 118 that illustrates a correct positioning of the heater bag 124 to assist the operator with correct placement of the heater bag 124, as shown in FIG. 11.

When the heater bag 124 is absent from the heater tray 116 during a treatment process (e.g., should the heater bag 124 be erroneously removed or otherwise become dislodged from the heater tray 116) such that the control unit 139 receives reference values from all of the force sensing elements 218, then the control unit 139 triggers an alarm to indicate to a patient or an operator that one or more actions should be performed to address the missing heater bag 124. Such actions can include stopping the treatment, appropriately placing the heater bag 124 atop the heater tray 116, restarting the treatment, and. The control unit 139 also sends a signal to the safety clamp to close off the patient line 130 to prevent dialysate fluid flow between the patient's abdominal cavity and the PD system 100. Upon a restart of the treatment process and a proper placement of the heater bag 124 atop the heater tray 116, the safety clamp disengages the patient line 130 to permit dialysate fluid flow in the patient line 130.

An arrangement of the force sensing elements 218 (e.g., laid out in a 2D array that spans the top surface 202 of the heater tray 116) can provide a weight distribution across the heater tray 116 that can advantageously be used to determine whether or not the heater bag 124 is appropriately placed atop the heater tray 116, whereas conventional weight scales used in other dialysis systems may be limited to merely providing a measurement of total weight atop a heater tray. In some implementations, determining an appropriate placement of the heater bag 124 in conjunction with determining the amount of dialysate within the heater bag 124 at any point in time can improve an overall assessment of the heater bag 124 and therefore streamline operator interaction with the PD system 100 during treatments. Such streamlined interaction can reduce inconveniences for a patient or an operator and accordingly minimize returns or troubleshooting of the PD system 100 that could otherwise occur.

Additionally, positioning of the force sensing elements 218 across the top surface of the heater tray 116 can advantageously remove the requirement for a conventional weight scale (e.g., a load cell) that may otherwise be disposed between the housing 106 (shown in FIG. 1) and the bracket 216 supporting the heater tray 116. Since such weight scales are often subject to shipping and handling damage, removal of such weight scales can significantly reduce the risk of damage to delicate components of the PD system 100 during transportation and any associated costs or inconveniences.

Figure 10:
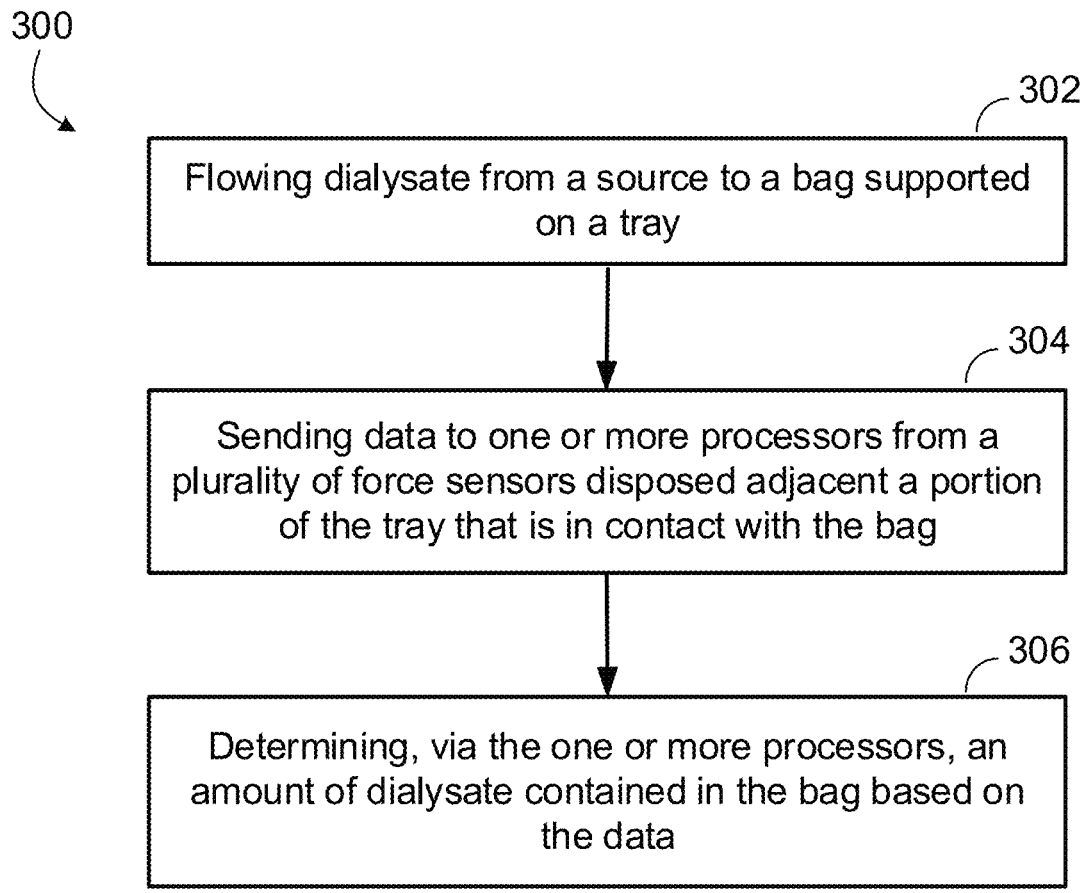
FIG. 10 is a flowchart showing a method of determining an amount of dialysate in a bag disposed atop the heater tray of FIGS. 4-7.

FIG. 10 is a flowchart showing a method 300 of determining an amount of dialysate within a heater bag disposed atop a heater tray of a PD system. In some implementations, dialysate is flowed from a source (e.g., one or more of the dialysate bags 122) to a bag (e.g., the heater bag 124) supported on a tray (e.g., the heater tray 116) (302). In some implementations, data is sent to one or more processors (e.g., one or more processors included within the control unit 139) from multiple force sensors (e.g., the force sensing elements 218) disposed adjacent a portion (e.g., the top surface 202) of the tray that is in contact with the bag (304). In some examples, the multiple force sensors can be arranged in an array that spans a majority of a cross-sectional area of the tray. For example, referring again to FIG. 4, the force sensing elements 218 span about 90% to about 95% of the total cross-sectional area of the heater tray 116. In some examples, the multiple force sensors are thin film sensors that are secured to the tray with an adhesive. In some examples, the multiple force sensors are attached to a top surface of the tray. In some examples, the multiple force sensors are disposed within a body of the tray adjacent a top surface of the tray. In some examples, the multiple force sensors are arranged to provide a weight distribution of dialysate within the bag across the tray.

In some implementations, the one or more processors execute instructions to determine an amount of dialysate contained in the bag based on the data (306). In some examples, the one or more processors are further configured to determine, based on the data, whether or not the bag is appropriately located on the tray. For example, the data may include output values corresponding to measurable weights from at least a threshold number of the multiple force sensors. In some examples, the one or more processors are further configured to determine, based on the data, whether or not the bag is supported by the tray. For example, the data may include output values from each of the multiple force sensors that are equal to a reference value that corresponds to an absence of a weight atop the heater tray.

In some examples, the one or more processors are configured to calculate the amount of dialysate contained in the bag from the data according to an algorithm. In some examples, the one or more processors are configured to determine the amount of dialysate contained in the bag by summing values included in the data. In some examples, the one or more processors are configured to compare the amount of dialysate to a reference amount. The one or more processors are further configured to trigger an alarm (e.g., a visual or an audio notification) if a difference between the amount of dialysate and the reference amount exceeds a threshold amount.

In some examples, the tray includes a heating element (e.g., the heating element 208) configured to heat the tray. For example, the tray is configured to conduct heat such that the tray heats the bag when the bag is supported by the tray. In some examples, the tray includes one or more temperature sensors (e.g., the temperature sensing elements 212, 214) configured to detect a temperature of the bag. In some examples, the tray defines a receptacle (e.g., the indentation 204) configured to receive the bag.

FIG. 11 is a block diagram of an example computer system 400. For example, referring to FIG. 1, the control unit 139 could be an example of the system 400 described here. The system 400 includes a processor 410, a memory 420, a storage device 430, and an input/output interface 440. Each of the components 410, 420, 430, and 440 can be interconnected, for example, using a system bus 450. The processor 410 is capable of processing instructions for execution within the system 400. The processor 410 can be a single-threaded processor, a multi-threaded processor, or a quantum computer. The processor 410 is capable of processing instructions stored in the memory 420 or on the storage device 430. The processor 410 may execute operations such as receiving signals from a sensing element (e.g., the temperature sensing element 212 shown in FIGS. 4 and 5) and comparing data based on the signals to stored data, e.g., data stored in a look-up table of temperature values.

The memory 420 stores information within the system 400. In some implementations, the memory 420 is a computer-readable medium. The memory 420 can, for example, be a volatile memory unit or a non-volatile memory unit. In some implementations, the memory 420 stores a data structure, such as one containing positional data for the force sensing elements 218. In some implementations, multiple data structures are used.

The storage device 430 is capable of providing mass storage for the system 400. In some implementations, the storage device 430 is a non-transitory computer-readable medium. The storage device 430 can include, for example, a hard disk device, an optical disk device, a solid-date drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the system 400. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices 118. In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 400. In some implementations, one or more sensing elements (e.g., the sensing elements 212, 214 shown in FIGS. 4 and 5) are in communication with the analog-to-digital converter 441. For example, if a sensing element includes at least one thermistor 442, the thermistor 442 can be placed in an electrical circuit with the analog-to-digital converter 441. In some implementations, the thermistor 442 is directly connected to the analog-to-digital converter 441, e.g., connected such that no other components are placed between the thermistor 442 and the analog-to-digital converter 441 in the electrical circuit. In some implementations, the thermistor 442 is not directly connected to the analog-to-digital converter 441. For example, the circuit containing the thermistor 442 and the analog-to-digital converter 441 could contain other components such as an operational amplifier and/or a buffer circuit. In some implementations, a differential amplifier circuit is placed in series between the thermistor 442 and an input lead of the analog-to-digital converter 441.

In some implementations, the system 400 is a microcontroller. A microcontroller is a device that contains multiple elements of a computer system in a single electronics package. For example, the single electronics package could contain the processor 410, the memory 420, the storage device 430, and input/output interfaces 440.

Although an example processing system has been described in FIG. 11, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disksand CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. For example, while the PD system 100 has been described and illustrated as including a mechanical connection between the piston heads 134A, 134B and the cassette 112, in some embodiments, a PD system that is otherwise substantially similar in construction and function to the PD system 100 may include piston heads 134A, 134B and a cassette 112 that are secured to each other with a vacuum pressure instead of a mechanical connection. In such implementations, for example, the cassette interface can include annular openings that at least partially surround the piston heads 134A, 134B and are connected to a vacuum system that can be used to draw a vacuum on the cassette membrane 140 to secure the cassette membrane 140 to the piston heads 134A, 134B. Accordingly, other embodiments are within the scope of the following claims.

What is claimed is:

1. A peritoneal dialysis system, comprising:
a tray for supporting a bag that can receive dialysate from a source of dialysate;
a plurality of force sensors disposed adjacent a portion of the tray that is in contact with the bag when the bag is supported by the tray; and
one or more processors configured to receive data from the plurality of force sensors and to calculate an amount of dialysate contained in the bag from the data according to an algorithm.

2. The peritoneal dialysis system of claim 1, wherein the plurality of force sensors are arranged in an array that spans a majority of a cross-sectional area of the tray.

3. The peritoneal dialysis system of claim 1, wherein the plurality of force sensors comprise thin film sensors that are secured to the tray with an adhesive.

4. The peritoneal dialysis system of claim 1, wherein the plurality of force sensors are attached to a top surface of the tray.

5. The peritoneal dialysis system of claim 1, wherein the plurality of force sensors are disposed within a body of the tray adjacent a top surface of the tray.

6. The peritoneal dialysis system of claim 1, wherein the plurality of force sensors are arranged to provide a weight distribution of dialysate within the bag across the tray.

7. The peritoneal dialysis system of claim 1, wherein the one or more processors are further configured to determine, based on the data, whether or not the bag is appropriately located on the tray.

8. The peritoneal dialysis system of claim 7, wherein the data comprises output values corresponding to measureable weights from at least a threshold number of the plurality of force sensors.

9. The peritoneal dialysis system of claim 1, wherein the one or more processors are further configured to determine, based on the data, whether or not the bag is supported by the tray.

10. The peritoneal dialysis system of claim 9, wherein the data comprises output values from each of the plurality of force sensors that are equal to a reference value.

11. The peritoneal dialysis system of claim 1, wherein the one or more processors are further configured to determine the amount of dialysate contained in the bag by summing values included in the data.

12. The peritoneal dialysis system of claim 1, wherein the one or more processors are further configured to compare the amount of dialysate to a reference amount.

13. The peritoneal dialysis system of claim 12, wherein the one or more processors are further configured to trigger an alarm if a difference between the amount of dialysate and the reference amount exceeds a threshold amount.

14. The peritoneal dialysis system of claim 13, wherein the alarm comprises a visual or an audio notification.

15. The peritoneal dialysis system of claim 1, wherein the tray comprises a heating element configured to heat the tray.

16. The peritoneal dialysis system of claim 15, wherein the tray is configured to conduct heat such that the tray heats the bag when the bag is supported by the tray.

17. The peritoneal dialysis system of claim 15, wherein the tray comprises one or more temperature sensors configured to detect a temperature of the bag.

18. The peritoneal dialysis system of claim 1, wherein the tray defines a receptacle configured to receive the bag.

19. The peritoneal dialysis system of claim 1, further comprising the source of dialysate.

20. A method of determining an amount of dialysate in a bag, the method comprising:
   flowing dialysate from a source to a bag supported on a tray;
   sending data to one or more processors from a plurality of force sensors disposed adjacent a portion of the tray that is in contact with the bag; and
   calculating, via the one or more processors, an amount of dialysate contained in the bag from the data according to an algorithm.

21. A peritoneal dialysis system, comprising:
   a tray for supporting a bag that can receive dialysate from a source of dialysate;
   a plurality of force sensors disposed adjacent a portion of the tray that is in contact with the bag when the bag is supported by the tray; and
   one or more processors configured to:
      receive data from the plurality of force sensors, the data comprising output values corresponding to measureable weights from at least a threshold number of the plurality of force sensors,
      determine, based on the data, an amount of dialysate contained in the bag, and
      determine, based on the data, whether or not the bag is appropriately located on the tray.

22. A peritoneal dialysis system, comprising:
   a tray for supporting a bag that can receive dialysate from a source of dialysate;
   a plurality of force sensors disposed adjacent a portion of the tray that is in contact with the bag when the bag is supported by the tray; and
   one or more processors configured to:
      receive data from the plurality of force sensors, the data comprising output values from each of the plurality of force sensors that are equal to a reference value,
      determine, based on the data, an amount of dialysate contained in the bag, and
      determine, based on the data, whether or not the bag is supported on the tray.

23. A peritoneal dialysis system, comprising:
   a tray for supporting a bag that can receive dialysate from a source of dialysate;
   a plurality of force sensors disposed adjacent a portion of the tray that is in contact with the bag when the bag is supported by the tray; and
   one or more processors configured to:
      receive data from the plurality of force sensors, and
      determine, based on the data, an amount of dialysate contained in the bag by summing values included in the data.

* * * * *